US010703799B2

(12) United States Patent
Beyaert et al.

(10) Patent No.: US 10,703,799 B2
(45) Date of Patent: Jul. 7, 2020

(54) IL-33R AND IL-1RACP FUSION PROTEINS

(71) Applicants: VIB VZW, Ghent (BE); Universiteit Gent, Ghent (BE)

(72) Inventors: Rudi Beyaert, Zingem (BE); Harald Braun, Ghent (BE); Bart Lambrecht, Laarne (BE); Hamida Hammad, Ronse (BE)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 0 days.

(21) Appl. No.: 14/649,526

(22) PCT Filed: Dec. 10, 2013

(86) PCT No.: PCT/EP2013/076082
§ 371 (c)(1),
(2) Date: Jun. 3, 2015

(87) PCT Pub. No.: WO2014/090800
PCT Pub. Date: Jun. 19, 2014

(65) Prior Publication Data
US 2015/0315262 A1 Nov. 5, 2015

(30) Foreign Application Priority Data
Dec. 10, 2012 (EP) .................................... 12196262

(51) Int. Cl.
*C07K 19/00* (2006.01)
*C07K 14/715* (2006.01)
*A61K 38/00* (2006.01)

(52) U.S. Cl.
CPC .......... *C07K 14/7155* (2013.01); *A61K 38/00* (2013.01); *C07K 2319/00* (2013.01); *C07K 2319/21* (2013.01); *C07K 2319/32* (2013.01); *C07K 2319/41* (2013.01)

(58) Field of Classification Search
None
See application file for complete search history.

(56) References Cited

U.S. PATENT DOCUMENTS

| 7,560,530 B1 | 7/2009 | Chackerian et al. |
| 8,187,596 B1 | 5/2012 | Chackerian et al. |
| 2002/0012962 A1* | 1/2002 | Stahl .................... C07K 14/715 435/69.1 |
| 2002/0052475 A1* | 5/2002 | Leung ................ C07K 14/7155 530/350 |
| 2003/0049255 A1 | 3/2003 | Sims et al. |
| 2005/0053579 A1* | 3/2005 | Galipeau ................ A61K 39/39 424/85.1 |
| 2005/0147618 A1* | 7/2005 | Rivera ............... A61K 47/4843 424/178.1 |
| 2005/0203046 A1 | 9/2005 | Schmitz et al. |
| 2007/0160579 A1 | 7/2007 | Schmitz et al. |
| 2009/0041718 A1 | 2/2009 | Schmitz et al. |
| 2012/0207752 A1 | 8/2012 | Chackerian et al. |
| 2012/0263709 A1 | 10/2012 | Rankin et al. |

FOREIGN PATENT DOCUMENTS

| WO | 2005079844 A2 | 9/2005 |
| WO | 2005079844 A3 | 11/2005 |
| WO | 2011031600 A1 | 3/2011 |
| WO | 2014090800 A1 | 6/2014 |

OTHER PUBLICATIONS

Kakkar et al. The IL-33/ST2 pathway: therapeutic target and novel biomarker. Nat Rev Drug Discov. Oct. 2008;7(10):827-40.*
Jensen L.E. Targeting the IL-1 family members in skin inflammation. Curr Opin Investig Drugs. Nov. 2010;11(11):1211-20.*
Leung Bernard P et al:, A novel therapy of murine collagen-induced arthritis with soluble T1/S12, the Journal of Immunology, the American Association of Immunologists, US, vol. 173, No. 1, Jul. 1, 2004 (Jul. 1, 2004), pp. 145-150.
Shafaqat Ali:, Characterization of Interleukin-33 and I L-33 Receptor Complex, Dissertation, Jul. 1, 2009 (Jul. 1, 2009), pp. 1-126.
Xiaoying Chen et al:, Fusion protein linkers: Property, design and functionality, Advanced Drug Delivery Reviews, Sep. 1, 2012 (Sep. 1, 2012).
Ali S et al: "Caspase 3 inactivates biologically active full length interleukin-33 as a classical cytokine but does not prohibit nuclear translocation", Biochemical and Biophysical Research Communications, Academic Press Inc. Orlando, FL, US, vol. 391, No. 3, Jan. 15, 2010 (Jan. 15, 2010), pp. 1512-1516.
Ali Shafaqat et al: "IL-1 receptor accessory protein is essential for IL-33-induced activation of T lymphocytes and mast cells", National Academy of Sciences. Proceedings, National Academy of Sciences, United States, vol. 104, No. 47, Nov. 20, 2007 (Nov. 20, 2007), pp. 18660-18665.

(Continued)

*Primary Examiner* — Dong Jiang

(74) *Attorney, Agent, or Firm* — Patent Law Works, LLP

(57) ABSTRACT

The present invention relates to novel inhibitors of IL-33. More specifically, it relates to a fusion protein of the soluble IL-33 receptor with the soluble IL-1RAcP as inhibitor of IL-33 activity. The invention relates further to the use of the inhibitor in treatment of IL-33-related diseases such as, but not limited to, asthma, atopic dermatitis and psoriasis.

4 Claims, 4 Drawing Sheets
Specification includes a Sequence Listing.

(56) References Cited

OTHER PUBLICATIONS

Palmer G et al: "The I L-1 receptor accessory protein (AcP) is required for IL1-33 signaling and soluble AcP enhances the ability of soluble ST2 to inhibit IL-33", Cytokine, Academic Press Ltd, Philadelphia, PA, US, vol. 42, No. 3, Jun. 1, 2008 (Jun. 1, 2008), pp. 358-364.
PCT International Search Report, PCT/EP2013/076082, dated Jan. 27, 2014.
Dinarello et al., Interleukin-18 and IL-18 binding protein, Frontiers in Immunology, Oct. 2013, pp. 1-10 vol. 4, Article 289.

\* cited by examiner

A

B

A

B

SEQUENCE LISTING

<160> NUMBER OF SEQ ID NOS: 21

<210> SEQ ID NO 1
<211> LENGTH: 763
<212> TYPE: PRT
<213> ORGANISM: artificial
<220> FEATURE:
<223> OTHER INFORMATION: mIL33trap (20xGGS)

<400> SEQUENCE: 1

```
Met Gly Leu Leu Trp Tyr Leu Met Ser Leu Ser Phe Tyr Gly Ile Leu
1               5                   10                  15

Gln Ser His Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Tyr Asn Tyr Ser Thr Ala His Ser Ser
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Ala Met Arg Phe
    130                 135                 140

Pro Val His Lys Met Tyr Ile Glu His Gly Ile His Lys Ile Thr Cys
145                 150                 155                 160

Pro Asn Val Asp Gly Tyr Phe Pro Ser Ser Val Lys Pro Ser Val Thr
                165                 170                 175

Trp Tyr Lys Gly Cys Thr Glu Ile Val Asp Phe His Asn Val Leu Pro
            180                 185                 190

Glu Gly Met Asn Leu Ser Phe Phe Ile Pro Leu Val Ser Asn Asn Gly
        195                 200                 205

Asn Tyr Thr Cys Val Val Thr Tyr Pro Glu Asn Gly Arg Leu Phe His
    210                 215                 220

Leu Thr Arg Thr Val Thr Val Lys Val Val Gly Ser Pro Lys Asp Ala
225                 230                 235                 240

Leu Pro Pro Gln Ile Tyr Ser Pro Asn Asp Arg Val Val Tyr Glu Lys
                245                 250                 255

Glu Pro Gly Glu Glu Leu Val Ile Pro Cys Lys Val Tyr Phe Ser Phe
            260                 265                 270

Ile Met Asp Ser His Asn Glu Val Trp Trp Thr Ile Asp Gly Lys Lys
        275                 280                 285

Pro Asp Asp Val Thr Val Asp Ile Thr Ile Asn Glu Ser Val Ser Tyr
    290                 295                 300

Ser Ser Thr Glu Asp Glu Thr Arg Thr Gln Ile Leu Ser Ile Lys Lys
305                 310                 315                 320

Val Thr Pro Glu Asp Leu Arg Arg Asn Tyr Val Cys His Ala Arg Asn
                325                 330                 335

Thr Lys Gly Glu Ala Glu Gln Ala Ala Lys Val Lys Gln Lys Gly Asn
```

-continued

```
                340                 345                 350
        Gly Cys Thr Glu Pro Met Thr Leu Ser Arg Gly Gly Ser Gly Gly Ser
                    355                 360                 365
        Gly Gly Ser Gly Gly Ser Gly Gly Ser Gly Gly Ser Gly Gly Ser Gly
            370                 375                 380
        Gly Ser Gly Gly Ser Gly Gly Ser Gly Gly Ser Gly Gly Ser Gly Gly
        385                 390                 395                 400
        Ser Gly Gly Ser Gly Gly Ser Gly Gly Ser Gly Gly Ser Gly Gly Ser
                    405                 410                 415
        Gly Gly Ser Gly Gly Ser Leu Gln Leu Gln Ser Lys Ser Ser Trp Gly
                    420                 425                 430
        Leu Glu Asn Glu Ala Leu Ile Val Arg Cys Pro Gln Arg Gly Arg Ser
                    435                 440                 445
        Thr Tyr Pro Val Glu Trp Tyr Tyr Ser Asp Thr Asn Glu Ser Ile Pro
                450                 455                 460
        Thr Gln Lys Arg Asn Arg Ile Phe Val Ser Arg Asp Arg Leu Lys Phe
        465                 470                 475                 480
        Leu Pro Ala Arg Val Glu Asp Ser Gly Ile Tyr Ala Cys Val Ile Arg
                        485                 490                 495
        Ser Pro Asn Leu Asn Lys Thr Gly Tyr Leu Asn Val Thr Ile His Lys
                        500                 505                 510
        Lys Pro Pro Ser Cys Asn Ile Pro Asp Tyr Leu Met Tyr Ser Thr Val
                    515                 520                 525
        Arg Gly Ser Asp Lys Asn Phe Lys Ile Thr Cys Pro Thr Ile Asp Leu
                    530                 535                 540
        Tyr Asn Trp Thr Ala Pro Val Gln Trp Phe Lys Asn Cys Lys Ala Leu
        545                 550                 555                 560
        Gln Glu Pro Arg Phe Arg Ala His Arg Ser Tyr Leu Phe Ile Asp Asn
                        565                 570                 575
        Val Thr His Asp Asp Glu Gly Asp Tyr Thr Cys Gln Phe Thr His Ala
                        580                 585                 590
        Glu Asn Gly Thr Asn Tyr Ile Val Thr Ala Thr Arg Ser Phe Thr Val
                    595                 600                 605
        Glu Glu Lys Gly Phe Ser Met Phe Pro Val Ile Thr Asn Pro Pro Tyr
                610                 615                 620
        Asn His Thr Met Glu Val Glu Ile Gly Lys Pro Ala Ser Ile Ala Cys
        625                 630                 635                 640
        Ser Ala Cys Phe Gly Lys Gly Ser His Phe Leu Ala Asp Val Leu Trp
                        645                 650                 655
        Gln Ile Asn Lys Thr Val Val Gly Asn Phe Gly Glu Ala Arg Ile Gln
                    660                 665                 670
        Glu Glu Glu Gly Arg Asn Glu Ser Ser Asn Asp Met Asp Cys Leu
                    675                 680                 685
        Thr Ser Val Leu Arg Ile Thr Gly Val Thr Glu Lys Asp Leu Ser Leu
                690                 695                 700
        Glu Tyr Asp Cys Leu Ala Leu Asn Leu His Gly Met Ile Arg His Thr
        705                 710                 715                 720
        Ile Arg Leu Arg Arg Lys Gln Pro Ser Lys Glu Cys Pro Ser His Ile
                        725                 730                 735
        Ala Ser Arg Gly Pro Phe Glu Gln Lys Leu Ile Ser Glu Glu Asp Leu
                    740                 745                 750
        Asn Met His Thr Gly His His His His His
                755                 760
```

<210> SEQ ID NO 2
<211> LENGTH: 737
<212> TYPE: PRT
<213> ORGANISM: artificial
<220> FEATURE:
<223> OTHER INFORMATION: mIL33trap (12xGGS)

<400> SEQUENCE: 2

Met Gly Leu Leu Trp Tyr Leu Met Ser Leu Ser Phe Tyr Gly Ile Leu
1               5                   10                  15

Gln Ser His Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Tyr Asn Tyr Ser Thr Ala His Ser Ser
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Ala Met Arg Phe
    130                 135                 140

Pro Val His Lys Met Tyr Ile Glu His Gly Ile His Lys Ile Thr Cys
145                 150                 155                 160

Pro Asn Val Asp Gly Tyr Phe Pro Ser Ser Val Lys Pro Ser Val Thr
                165                 170                 175

Trp Tyr Lys Gly Cys Thr Glu Ile Val Asp Phe His Asn Val Leu Pro
            180                 185                 190

Glu Gly Met Asn Leu Ser Phe Phe Ile Pro Leu Val Ser Asn Asn Gly
        195                 200                 205

Asn Tyr Thr Cys Val Val Thr Tyr Pro Glu Asn Gly Arg Leu Phe His
    210                 215                 220

Leu Thr Arg Thr Val Thr Val Lys Val Val Gly Ser Pro Lys Asp Ala
225                 230                 235                 240

Leu Pro Pro Gln Ile Tyr Ser Pro Asn Asp Arg Val Val Tyr Glu Lys
                245                 250                 255

Glu Pro Gly Glu Glu Leu Val Ile Pro Cys Lys Val Tyr Phe Ser Phe
            260                 265                 270

Ile Met Asp Ser His Asn Glu Val Trp Trp Thr Ile Asp Gly Lys Lys
        275                 280                 285

Pro Asp Asp Val Thr Val Asp Ile Thr Ile Asn Glu Ser Val Ser Tyr
    290                 295                 300

Ser Ser Thr Glu Asp Glu Thr Arg Thr Gln Ile Leu Ser Ile Lys Lys
305                 310                 315                 320

Val Thr Pro Glu Asp Leu Arg Arg Asn Tyr Val Cys His Ala Arg Asn
                325                 330                 335

Thr Lys Gly Glu Ala Glu Gln Ala Ala Lys Val Lys Gln Lys Gly Asn
            340                 345                 350

Gly Cys Thr Glu Pro Met Thr Leu Ser Arg Gly Gly Ser Gly Gly Ser
        355                 360                 365

Gly Gly Ser Gly Gly Ser Gly Gly Ser Gly Gly Ser Gly
            370             375             380
Gly Ser Gly Gly Ser Gly Gly Ser Gly Gly Ser Gly Gly Ser Leu Gln
385             390             395             400
Ser Lys Ser Ser Trp Gly Leu Glu Asn Glu Ala Leu Ile Val Arg Cys
            405             410             415
Pro Gln Arg Gly Arg Ser Thr Tyr Pro Val Glu Trp Tyr Tyr Ser Asp
            420             425             430
Thr Asn Glu Ser Ile Pro Thr Gln Lys Arg Asn Arg Ile Phe Val Ser
            435             440             445
Arg Asp Arg Leu Lys Phe Leu Pro Ala Arg Val Glu Asp Ser Gly Ile
450             455             460
Tyr Ala Cys Val Ile Arg Ser Pro Asn Leu Asn Lys Thr Gly Tyr Leu
465             470             475             480
Asn Val Thr Ile His Lys Lys Pro Pro Ser Cys Asn Ile Pro Asp Tyr
            485             490             495
Leu Met Tyr Ser Thr Val Arg Gly Ser Asp Lys Asn Phe Lys Ile Thr
            500             505             510
Cys Pro Thr Ile Asp Leu Tyr Asn Trp Thr Ala Pro Val Gln Trp Phe
            515             520             525
Lys Asn Cys Lys Ala Leu Gln Glu Pro Arg Phe Arg Ala His Arg Ser
530             535             540
Tyr Leu Phe Ile Asp Asn Val Thr His Asp Asp Glu Gly Asp Tyr Thr
545             550             555             560
Cys Gln Phe Thr His Ala Glu Asn Gly Thr Asn Tyr Ile Val Thr Ala
            565             570             575
Thr Arg Ser Phe Thr Val Glu Glu Lys Gly Phe Ser Met Phe Pro Val
            580             585             590
Ile Thr Asn Pro Pro Tyr Asn His Thr Met Glu Val Glu Ile Gly Lys
            595             600             605
Pro Ala Ser Ile Ala Cys Ser Ala Cys Phe Gly Lys Gly Ser His Phe
610             615             620
Leu Ala Asp Val Leu Trp Gln Ile Asn Lys Thr Val Val Gly Asn Phe
625             630             635             640
Gly Glu Ala Arg Ile Gln Glu Glu Gly Arg Asn Glu Ser Ser Ser
            645             650             655
Asn Asp Met Asp Cys Leu Thr Ser Val Leu Arg Ile Thr Gly Val Thr
            660             665             670
Glu Lys Asp Leu Ser Leu Glu Tyr Asp Cys Leu Ala Leu Asn Leu His
            675             680             685
Gly Met Ile Arg His Thr Ile Arg Leu Arg Arg Lys Gln Pro Ser Lys
690             695             700
Glu Cys Pro Ser His Ile Ala Ser Arg Gly Pro Phe Glu Gln Lys Leu
705             710             715             720
Ile Ser Glu Glu Asp Leu Asn Met His Thr Gly His His His His
            725             730             735
His

<210> SEQ ID NO 3
<211> LENGTH: 727
<212> TYPE: PRT
<213> ORGANISM: artificial
<220> FEATURE:
<223> OTHER INFORMATION: mIL33trap (8xGGS)

<400> SEQUENCE: 3

```
Met Gly Leu Leu Trp Tyr Leu Met Ser Leu Ser Phe Tyr Gly Ile Leu
1               5                   10                  15

Gln Ser His Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Tyr Asn Tyr Ser Thr Ala His Ser Ser
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
            85                  90                  95

Asp Val Leu Trp Phe Arg Pro Thr Leu Leu Asn Asp Thr Gly Asn Tyr
        100                 105                 110

Thr Cys Met Leu Arg Asn Thr Thr Tyr Cys Ser Lys Val Ala Phe Pro
    115                 120                 125

Leu Glu Val Val Gln Lys Asp Ser Cys Phe Asn Ser Ala Met Arg Phe
130                 135                 140

Pro Val His Lys Met Tyr Ile Glu His Gly Ile His Lys Ile Thr Cys
145                 150                 155                 160

Pro Asn Val Asp Gly Tyr Phe Pro Ser Ser Val Lys Pro Ser Val Thr
            165                 170                 175

Trp Tyr Lys Gly Cys Thr Glu Ile Val Asp Phe His Asn Val Leu Pro
        180                 185                 190

Glu Gly Met Asn Leu Ser Phe Phe Ile Pro Leu Val Ser Asn Asn Gly
    195                 200                 205

Asn Tyr Thr Cys Val Val Thr Tyr Pro Glu Asn Gly Arg Leu Phe His
210                 215                 220

Leu Thr Arg Thr Val Thr Val Lys Val Val Gly Ser Pro Lys Asp Ala
225                 230                 235                 240

Leu Pro Pro Gln Ile Tyr Ser Pro Asn Asp Arg Val Val Tyr Glu Lys
            245                 250                 255

Glu Pro Gly Glu Glu Leu Val Ile Pro Cys Lys Val Tyr Phe Ser Phe
        260                 265                 270

Ile Met Asp Ser His Asn Glu Val Trp Trp Thr Ile Asp Gly Lys Lys
    275                 280                 285

Pro Asp Asp Val Thr Val Asp Ile Thr Ile Asn Glu Ser Val Ser Tyr
290                 295                 300

Ser Ser Thr Glu Asp Glu Thr Arg Thr Gln Ile Leu Ser Ile Lys Lys
305                 310                 315                 320

Val Thr Pro Glu Asp Leu Arg Arg Asn Tyr Val Cys His Ala Arg Asn
            325                 330                 335

Thr Lys Gly Glu Ala Glu Gln Ala Ala Lys Val Lys Gln Lys Gly Asn
        340                 345                 350

Gly Cys Thr Glu Pro Met Thr Leu Ser Arg Gly Gly Ser Gly Gly Ser
    355                 360                 365

Gly Gly Ser Gly Gly Ser Gly Gly Ser Gly Gly Ser Gly Gly Ser Gly
370                 375                 380

Gly Ser Leu Gln Leu Gln Ser Lys Ser Ser Trp Gly Leu Glu Asn Glu
385                 390                 395                 400

Ala Leu Ile Val Arg Cys Pro Gln Arg Gly Arg Ser Thr Tyr Pro Val
```

```
            405                 410                 415
Glu Trp Tyr Tyr Ser Asp Thr Asn Glu Ser Ile Pro Thr Gln Lys Arg
            420                 425                 430

Asn Arg Ile Phe Val Ser Arg Asp Arg Leu Lys Phe Leu Pro Ala Arg
        435                 440                 445

Val Glu Asp Ser Gly Ile Tyr Ala Cys Val Ile Arg Ser Pro Asn Leu
    450                 455                 460

Asn Lys Thr Gly Tyr Leu Asn Val Thr Ile His Lys Lys Pro Pro Ser
465                 470                 475                 480

Cys Asn Ile Pro Asp Tyr Leu Met Tyr Ser Thr Val Arg Gly Ser Asp
                485                 490                 495

Lys Asn Phe Lys Ile Thr Cys Pro Thr Ile Asp Leu Tyr Asn Trp Thr
            500                 505                 510

Ala Pro Val Gln Trp Phe Lys Asn Cys Lys Ala Leu Gln Glu Pro Arg
        515                 520                 525

Phe Arg Ala His Arg Ser Tyr Leu Phe Ile Asp Asn Val Thr His Asp
    530                 535                 540

Asp Glu Gly Asp Tyr Thr Cys Gln Phe Thr His Ala Glu Asn Gly Thr
545                 550                 555                 560

Asn Tyr Ile Val Thr Ala Thr Arg Ser Phe Thr Val Glu Glu Lys Gly
                565                 570                 575

Phe Ser Met Phe Pro Val Ile Thr Asn Pro Pro Tyr Asn His Thr Met
            580                 585                 590

Glu Val Glu Ile Gly Lys Pro Ala Ser Ile Ala Cys Ser Ala Cys Phe
        595                 600                 605

Gly Lys Gly Ser His Phe Leu Ala Asp Val Leu Trp Gln Ile Asn Lys
    610                 615                 620

Thr Val Val Gly Asn Phe Gly Glu Ala Arg Ile Gln Glu Glu Glu Gly
625                 630                 635                 640

Arg Asn Glu Ser Ser Asn Asp Met Asp Cys Leu Thr Ser Val Leu
                645                 650                 655

Arg Ile Thr Gly Val Thr Glu Lys Asp Leu Ser Leu Glu Tyr Asp Cys
            660                 665                 670

Leu Ala Leu Asn Leu His Gly Met Ile Arg His Thr Ile Arg Leu Arg
        675                 680                 685

Arg Lys Gln Pro Ser Lys Glu Cys Pro Ser His Ile Ala Ser Arg Gly
    690                 695                 700

Pro Phe Glu Gln Lys Leu Ile Ser Glu Glu Asp Leu Asn Met His Thr
705                 710                 715                 720

Gly His His His His His His
                725

<210> SEQ ID NO 4
<211> LENGTH: 359
<212> TYPE: PRT
<213> ORGANISM: homo sapiens

<400> SEQUENCE: 4

Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
                20                  25                  30

Ile Val Arg Cys Pro Arg Gln Gly Lys Pro Ser Tyr Thr Val Asp Trp
            35                  40                  45
```

Tyr Tyr Ser Gln Thr Asn Lys Ser Ile Pro Thr Gln Glu Arg Asn Arg
 50                  55                  60

Val Phe Ala Ser Gly Gln Leu Leu Lys Phe Leu Pro Ala Ala Val Ala
 65                  70                  75                  80

Asp Ser Gly Ile Tyr Thr Cys Ile Val Arg Ser Pro Thr Phe Asn Arg
                 85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
            260                 265                 270

Asn Gln Ser Phe Ser Asn Gly Leu Ala Cys Leu Asp Met Val Leu Arg
        275                 280                 285

Ile Ala Asp Val Lys Glu Glu Asp Leu Leu Leu Gln Tyr Asp Cys Leu
290                 295                 300

Ala Leu Asn Leu His Gly Leu Arg Arg His Thr Val Arg Leu Ser Arg
305                 310                 315                 320

Lys Asn Pro Ser Lys Glu Cys Phe Ser Arg Pro Leu Glu Ser Arg Gly
                325                 330                 335

Pro Phe Glu Gln Lys Leu Ile Ser Glu Glu Asp Leu Asn Met His Thr
            340                 345                 350

Gly His His His His His His
        355

<210> SEQ ID NO 5
<211> LENGTH: 382
<212> TYPE: PRT
<213> ORGANISM: Homo sapiens

<400> SEQUENCE: 5

Met Thr Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
                 20                  25                  30

Arg Gln Ile Gln Val Phe Glu Asp Glu Pro Ala Arg Ile Lys Cys Pro
            35                  40                  45

Leu Phe Glu His Phe Leu Lys Phe Asn Tyr Ser Thr Ala His Ser Ala
        50                  55                  60

Gly Leu Thr Leu Ile Trp Tyr Trp Thr Arg Gln Asp Arg Asp Leu Glu
 65                  70                  75                  80

Glu Pro Ile Asn Phe Arg Leu Pro Glu Asn Arg Ile Ser Lys Glu Lys
                 85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Gly Asn
            340                 345                 350

Arg Cys Gly Gln Ser Arg Gly Pro Phe Glu Gln Lys Leu Ile Ser Glu
        355                 360                 365

Glu Asp Leu Asn Met His Thr Gly His His His His His His
370                 375                 380

<210> SEQ ID NO 6
<211> LENGTH: 761
<212> TYPE: PRT
<213> ORGANISM: Artificial Sequence
<220> FEATURE:
<223> OTHER INFORMATION: Fusion protein

<400> SEQUENCE: 6

Met Thr Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
                20                  25                  30

Arg Gln Ile Gln Val Phe Glu Asp Glu Pro Ala Arg Ile Lys Cys Pro
         35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                    85                  90                  95

Asp Val Leu Trp Phe Arg Pro Thr Leu Leu Asn Asp Thr Gly Asn Tyr
                100                 105                 110

Thr Cys Met Leu Arg Asn Thr Thr Tyr Cys Ser Lys Val Ala Phe Pro
            115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Gly Asn
            340                 345                 350

Arg Cys Gly Gln Ser Arg Gly Gly Ser Gly Gly Ser Gly
        355                 360                 365

Gly Ser Gly Gly Ser Gly Gly Ser Gly Gly Ser Gly Gly Ser Gly Gly
    370                 375                 380

Ser Gly Gly Ser Gly Gly Ser Gly Gly Ser Gly Gly Ser Gly Gly Ser
385                 390                 395                 400

Gly Gly Ser Gly Gly Ser Gly Gly Ser Gly Gly Ser Gly Gly Ser Gly
                405                 410                 415

Gly Ser Leu His Lys Phe Ser Lys Gln Ser Trp Gly Leu Glu Asn Glu
            420                 425                 430

Ala Leu Ile Val Arg Cys Pro Arg Gln Gly Lys Pro Ser Tyr Thr Val
        435                 440                 445

Asp Trp Tyr Tyr Ser Gln Thr Asn Lys Ser Ile Pro Thr Gln Glu Arg
    450                 455                 460

Asn Arg Val Phe Ala Ser Gly Gln Leu Leu Lys Phe Leu Pro Ala Ala
465                 470                 475                 480

Val Ala Asp Ser Gly Ile Tyr Thr Cys Ile Val Arg Ser Pro Thr Phe
            485                 490                 495

Asn Arg Thr Gly Tyr Ala Asn Val Thr Ile Tyr Lys Lys Gln Ser Asp
            500                 505                 510

Cys Asn Val Pro Asp Tyr Leu Met Tyr Ser Thr Val Ser Gly Ser Glu
            515                 520                 525

Lys Asn Ser Lys Ile Tyr Cys Pro Thr Ile Asp Leu Tyr Asn Trp Thr
530                 535                 540

Ala Pro Leu Glu Trp Phe Lys Asn Cys Gln Ala Leu Gln Gly Ser Arg
545                 550                 555                 560

Tyr Arg Ala His Lys Ser Phe Leu Val Ile Asp Asn Val Met Thr Glu
            565                 570                 575

Asp Ala Gly Asp Tyr Thr Cys Lys Phe Ile His Asn Glu Asn Gly Ala
            580                 585                 590

Asn Tyr Ser Val Thr Ala Thr Arg Ser Phe Thr Val Lys Asp Glu Gln
            595                 600                 605

Gly Phe Ser Leu Phe Pro Val Ile Gly Ala Pro Ala Gln Asn Glu Ile
610                 615                 620

Lys Glu Val Glu Ile Gly Lys Asn Ala Asn Leu Thr Cys Ser Ala Cys
625                 630                 635                 640

Phe Gly Lys Gly Thr Gln Phe Leu Ala Ala Val Leu Trp Gln Leu Asn
            645                 650                 655

Gly Thr Lys Ile Thr Asp Phe Gly Glu Pro Arg Ile Gln Gln Glu Glu
            660                 665                 670

Gly Gln Asn Gln Ser Phe Ser Asn Gly Leu Ala Cys Leu Asp Met Val
            675                 680                 685

Leu Arg Ile Ala Asp Val Lys Glu Glu Asp Leu Leu Leu Gln Tyr Asp
690                 695                 700

Cys Leu Ala Leu Asn Leu His Gly Leu Arg Arg His Thr Val Arg Leu
705                 710                 715                 720

Ser Arg Lys Asn Pro Ser Lys Glu Cys Phe Ser Arg Pro Leu Glu Ser
            725                 730                 735

Arg Gly Pro Phe Glu Gln Lys Leu Ile Ser Glu Glu Asp Leu Asn Met
            740                 745                 750

His Thr Gly His His His His His His
            755                 760

<210> SEQ ID NO 7
<211> LENGTH: 725
<212> TYPE: PRT
<213> ORGANISM: Artificial Sequence
<220> FEATURE:
<223> OTHER INFORMATION: Fusion protein

<400> SEQUENCE: 7

Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

```
Gly Leu Thr Leu Ile Trp Tyr Trp Thr Arg Gln Asp Arg Asp Leu Glu
 65                  70                  75                  80

Glu Pro Ile Asn Phe Arg Leu Pro Glu Asn Arg Ile Ser Lys Glu Lys
                 85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Gly Asn
            340                 345                 350

Arg Cys Gly Gln Ser Arg Gly Gly Ser Gly Gly Ser Gly Gly Ser Gly
        355                 360                 365

Gly Ser Gly Gly Ser Gly Gly Ser Gly Gly Ser Leu His
    370                 375                 380

Lys Phe Ser Lys Gln Ser Trp Gly Leu Glu Asn Glu Ala Leu Ile Val
385                 390                 395                 400

Arg Cys Pro Arg Gln Gly Lys Pro Ser Tyr Thr Val Asp Trp Tyr Tyr
                405                 410                 415

Ser Gln Thr Asn Lys Ser Ile Pro Thr Gln Glu Arg Asn Arg Val Phe
            420                 425                 430

Ala Ser Gly Gln Leu Leu Lys Phe Leu Pro Ala Ala Val Ala Asp Ser
        435                 440                 445

Gly Ile Tyr Thr Cys Ile Val Arg Ser Pro Thr Phe Asn Arg Thr Gly
    450                 455                 460

Tyr Ala Asn Val Thr Ile Tyr Lys Lys Gln Ser Asp Cys Asn Val Pro
465                 470                 475                 480

Asp Tyr Leu Met Tyr Ser Thr Val Ser Gly Ser Glu Lys Asn Ser Lys
```

```
                485                 490                 495
Ile Tyr Cys Pro Thr Ile Asp Leu Tyr Asn Trp Thr Ala Pro Leu Glu
            500                 505                 510

Trp Phe Lys Asn Cys Gln Ala Leu Gln Gly Ser Arg Tyr Arg Ala His
        515                 520                 525

Lys Ser Phe Leu Val Ile Asp Asn Val Met Thr Glu Asp Ala Gly Asp
    530                 535                 540

Tyr Thr Cys Lys Phe Ile His Asn Glu Asn Gly Ala Asn Tyr Ser Val
545                 550                 555                 560

Thr Ala Thr Arg Ser Phe Thr Val Lys Asp Glu Gln Gly Phe Ser Leu
                565                 570                 575

Phe Pro Val Ile Gly Ala Pro Ala Gln Asn Glu Ile Lys Glu Val Glu
            580                 585                 590

Ile Gly Lys Asn Ala Asn Leu Thr Cys Ser Ala Cys Phe Gly Lys Gly
        595                 600                 605

Thr Gln Phe Leu Ala Ala Val Leu Trp Gln Leu Asn Gly Thr Lys Ile
    610                 615                 620

Thr Asp Phe Gly Glu Pro Arg Ile Gln Gln Glu Gly Gln Asn Gln
625                 630                 635                 640

Ser Phe Ser Asn Gly Leu Ala Cys Leu Asp Met Val Leu Arg Ile Ala
                645                 650                 655

Asp Val Lys Glu Glu Asp Leu Leu Leu Gln Tyr Asp Cys Leu Ala Leu
            660                 665                 670

Asn Leu His Gly Leu Arg Arg His Thr Val Arg Leu Ser Arg Lys Asn
        675                 680                 685

Pro Ser Lys Glu Cys Phe Ser Arg Pro Leu Glu Ser Arg Gly Pro Phe
    690                 695                 700

Glu Gln Lys Leu Ile Ser Glu Glu Asp Leu Asn Met His Thr Gly His
705                 710                 715                 720

His His His His His
            725

<210> SEQ ID NO 8
<211> LENGTH: 31
<212> TYPE: DNA
<213> ORGANISM: artificial
<220> FEATURE:
<223> OTHER INFORMATION: Primer

<400> SEQUENCE: 8
agttctagaa tgattgacag acagagaatg g                              31

<210> SEQ ID NO 9
<211> LENGTH: 30
<212> TYPE: DNA
<213> ORGANISM: artificial
<220> FEATURE:
<223> OTHER INFORMATION: Primer

<400> SEQUENCE: 9
taatctagaa gcaatgtgtg agggacactc                                30

<210> SEQ ID NO 10
<211> LENGTH: 32
<212> TYPE: DNA
<213> ORGANISM: artificial
<220> FEATURE:
<223> OTHER INFORMATION: Primer
```

<400> SEQUENCE: 10
aattctagaa aagtgtttca ggtctaagca tg                                   32

<210> SEQ ID NO 11
<211> LENGTH: 30
<212> TYPE: DNA
<213> ORGANISM: artificial
<220> FEATURE:
<223> OTHER INFORMATION: Primer

<400> SEQUENCE: 11
ttcgaattca tgggacttct gtggtatttg                                       30

<210> SEQ ID NO 12
<211> LENGTH: 28
<212> TYPE: DNA
<213> ORGANISM: artificial
<220> FEATURE:
<223> OTHER INFORMATION: Primer

<400> SEQUENCE: 12
agatctagac agagtcatcg gctcggtg                                         28

<210> SEQ ID NO 13
<211> LENGTH: 30
<212> TYPE: DNA
<213> ORGANISM: artificial
<220> FEATURE:
<223> OTHER INFORMATION: Primer

<400> SEQUENCE: 13
cagctgcaga gtaaatcgtc ctggggtctg                                       30

<210> SEQ ID NO 14
<211> LENGTH: 32
<212> TYPE: DNA
<213> ORGANISM: artificial
<220> FEATURE:
<223> OTHER INFORMATION: Primer

<400> SEQUENCE: 14
atcgatatcg tttaaactca atggtgatgg tg                                   32

<210> SEQ ID NO 15
<211> LENGTH: 29
<212> TYPE: DNA
<213> ORGANISM: artificial
<220> FEATURE:
<223> OTHER INFORMATION: Primer

<400> SEQUENCE: 15
agatctagag gagggagtgg tggctctgg                                        29

<210> SEQ ID NO 16
<211> LENGTH: 29
<212> TYPE: DNA
<213> ORGANISM: artificial
<220> FEATURE:
<223> OTHER INFORMATION: Primer

<400> SEQUENCE: 16
cagctgcagg ctcccaccac tccctccag                                        29

<210> SEQ ID NO 17
<211> LENGTH: 34

```
<212> TYPE: DNA
<213> ORGANISM: artificial
<220> FEATURE:
<223> OTHER INFORMATION: Primer

<400> SEQUENCE: 17
tccggatcca tggggttttg gatcttagca attc                              34

<210> SEQ ID NO 18
<211> LENGTH: 38
<212> TYPE: DNA
<213> ORGANISM: artificial
<220> FEATURE:
<223> OTHER INFORMATION: Primer

<400> SEQUENCE: 18
taagcggccg cgagaaacac tccttacttg gatttttc                          38

<210> SEQ ID NO 19
<211> LENGTH: 33
<212> TYPE: DNA
<213> ORGANISM: artificial
<220> FEATURE:
<223> OTHER INFORMATION: Primer

<400> SEQUENCE: 19
ttcgaattca tgacacttct gtggtgtgta gtg                               33

<210> SEQ ID NO 20
<211> LENGTH: 33
<212> TYPE: DNA
<213> ORGANISM: artificial
<220> FEATURE:
<223> OTHER INFORMATION: Primer

<400> SEQUENCE: 20
atttctagac tgaccgcatc tattaccttt ctg                               33

<210> SEQ ID NO 21
<211> LENGTH: 32
<212> TYPE: DNA
<213> ORGANISM: artificial
<220> FEATURE:
<223> OTHER INFORMATION: Primer

<400> SEQUENCE: 21
catatgcata agtttagtaa acaatcatgg gg                                32
```

IL-33R AND IL-1RACP FUSION PROTEINS

CROSS-REFERENCE TO RELATED APPLICATIONS

This application is a national phase entry under 35 U.S.C. § 371 of International Patent Application PCT/EP2013/076082, filed Dec. 10, 2013, designating the United States of America and published in English as International Patent Publication WO 2014/090800 A1 on Jun. 19, 2014, which claims the benefit under Article 8 of the Patent Cooperation Treaty and under 35 U.S.C. § 119(e) to European Patent Application Serial No. 12196262.5, filed Dec. 10, 2012.

TECHNICAL FIELD

This disclosure relates to novel inhibitors of Interleukin-33 (IL-33). More specifically, it relates to a fusion protein comprising the soluble IL-33 receptor and the soluble Interleukin-1 receptor accessory protein (IL-1RAcP) as inhibitor of IL-33 activity. The disclosure relates further to the use of the inhibitor in treatment of IL-33-related diseases such as, but not limited to, asthma, atopic dermatitis and psoriasis.

BACKGROUND

Interleukin-33 (IL-33), also known as IL-1F11 or DVS27, is a member of the IL-1 superfamily of cytokines that is expressed mainly in stromal cells, such as epithelial and endothelial cells. The IL-1 family members and the IL-1 receptor family play an important role in inflammatory and immunological responses. IL-1 superfamily-related diseases include asthma, chronic obstructive pulmonary disorder (COPD), rheumatoid arthritis and psoriasis. IL-1 receptors have been used in the treatment of diseases. U.S. 2003/0049255 discloses a method of treating a patient affected with a medical disorder selected from the group consisting of rheumatoid arthritis, Alzheimer's, stroke, head trauma, myocardial infarction, heart failure, periodontal disease, inflammatory bowel disease, asthma and pancreatitis by administering a therapeutically effective amount of an IL-1 receptor and Interleukin-1 receptor accessory protein (IL-1RAcP), wherein IL-1RAcP may be soluble IL1-RAcP.

IL-33 plays a role in inflammation and several diseases, including asthma, rheumatologic diseases, inflammatory skin disorders, inflammatory bowel disease, central nervous inflammation, cancer, cardiovascular diseases (for a review, see Miller, 2011).

IL-33 seems to be a cytokine with a dual function, acting both as traditional cytokine and as intracellular nuclear factor with transcriptional regulatory properties (Haraldsen et al., 2009). IL-33 acts as a cytokine by binding to the ST2L/IL-1RAcP receptor complex (Chackerian et al. 2007). Signaling is then induced through the cytoplasmic Toll-interleukin receptor domain of IL-1RAcP.

IL-33 differs from other IL-1 family members by primarily inducing T helper 2 (Th2) immune responses in a number of immune cell types (Lamkanfi and Dixit, 2009).

In view of its important role in diseases, several strategies have been proposed to control pathogenic IL-33 expression. WO 2005/079844 discloses IL-33 antagonists, consisting of IL-33 or IL-33 receptor antibodies. Leung et al. (2004) describes a therapy of murine collagen-induced arthritis with soluble ST2, but they did not study the effect of the soluble receptor on IL-33. Hayakawa et al. (2007) shows that soluble ST2 blocks IL-33 signaling in allergic airway inflammation. However, although some improvement is obtained with these approaches, the blocking of the IL-33 response is rather weak and there is a need for better and stronger antagonists.

Surprisingly, it was found that a fusion protein comprising the soluble IL-33 receptor and the soluble IL-1RAcP efficiently inhibits the IL-33 response. The inhibition is not only stronger than the inhibition caused by soluble IL-33 receptor or by soluble IL-1RAcP alone, it is surprisingly also more efficient than a mixture of both soluble receptors.

DISCLOSURE

Therefore, a first aspect of the disclosure is a fusion protein (also referred to as IL-33trap) comprising the soluble IL-33 receptor and the soluble IL-1RAcP. The soluble IL-33 receptor and the soluble IL-1RAcP are known to the person skilled in the art. Preferably, the soluble IL-33 receptor is the human soluble IL-33 receptor (SEQ ID NO:4) and the soluble IL-1RAcP is the human soluble IL-1RAcP (SEQ ID NO:5). Alternatively, a homologue of those polypeptides may be used. "Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. The terms "protein" and "polypeptide" as used in this application are interchangeable. Polypeptide refers to a polymer of amino acids and does not refer to a specific length of the molecule. This term also includes post-translational modifications of the polypeptide, such as glycosylation, phosphorylation and acetylation. The fusion may be at the aminoterminal or at the carboxyterminal end of the soluble IL-33 receptor. Preferably, both soluble polypeptides are linked with a linker. Even more preferably, the linker is at least ten amino acids in length. More preferably, the linker consists of GGS repeats, most preferably at least eight GGS repeats up to thirty GGS repeats. Preferably, the linker consists of at least ten GGS repeats, even more preferably, at least twenty GGS repeats. Most preferably, the fusion protein comprises a sequence selected from the group consisting of SEQ ID NO:1, SEQ ID NO:2, and SEQ ID NO:3. Alternatively, the fusion protein comprises the human homologues, as represented in SEQ ID NO:6, and SEQ ID NO:7.

Another aspect of the disclosure is the use of a fusion protein according to the disclosure as a medicament. Still another aspect of the disclosure is a fusion protein according to the disclosure for use in an IL-33-related disease. IL-33-related diseases are known to the person skilled in the art, and include, but are not limited to, asthma, rheumatoid arthritis, osteoarthritis, atopic dermatitis, psoriasis, psoriatic arthritis, systemic lupus erythematosus, inflammatory skin disorders, inflammatory bowel disease and cancer. One preferred embodiment is the fusion protein for use in treatment of asthma. Another preferred embodiment is the fusion protein for use in treatment of atopic dermatitis. Another preferred embodiment is the fusion protein for use in treatment of psoriasis. Another preferred embodiment is the fusion protein for use in treatment of rheumatoid arthritis. Still another preferred embodiment is the fusion protein for use in inflammatory bowel disease.

Still another aspect of the disclosure is the use of a fusion protein according to the disclosure for the preparation of a medicament, preferably for the preparation of a medicament to treat an IL-33-related disease, as described above.

Another aspect of the disclosure is a pharmaceutical composition comprising a fusion protein according to the disclosure, optionally with a suitable excipient. Suitable excipients are known to the person skilled in the art and are inherently non-toxic and non-therapeutic. Excipients may be, as a non-limiting example, Ringer's solution, dextrose solution or Hank's solution. Non-aqueous solutions such as fixed oils and ethyl oleate may also be used. A preferred excipient is 5% dextrose in saline. The excipient may contain minor amounts of additives such as substances that enhance isotonicity and chemical stability, including buffers and preservatives.

Another aspect of the disclosure is the use of a fusion protein according to the disclosure to inhibit IL-33 signaling.

Still another aspect of the disclosure is a method to treat an IL-33-related disease, as described above, the method comprising: (i) providing a pharmaceutical composition according to the disclosure, and (ii) applying a suitable amount of the pharmaceutical composition to a patient in need of the treatment.

DETAILED DESCRIPTION

Examples

Materials and Methods to the Examples

Figure 1:
FIG. 1: Engineered IL-33 trap. Panel A, Schematic representation of the engineered IL-33 trap. The soluble IL-1RAcP receptor ("SmIL-1RAcP") is fused to the soluble ST2 receptor ("mST2s"). Both receptor components are separated by a flexible linker consisting of Gly-Gly-Ser repeats ("GGS-linker"). The signal peptide at the N-terminus ensures secretion of the expressed protein into the medium fraction. A carboxy terminal myc/His6 tag (black) is used for detection and purification. Panel B, Western blot analysis of secreted proteins. Conditioned medium from HEK293T cells transiently transfected with empty vector (lane 1), pEF-SmIL1RAcP (lane 2), pEF-mST2s (lane 3) or pEF-mIL33trap (lane 4) were analyzed by Western blotting with an anti-His6 antibody. Protein size is indicated in kDa at the left. Due to glycosylation of the expressed proteins, the apparent size is bigger than their theoretical weight.
Figure 1:
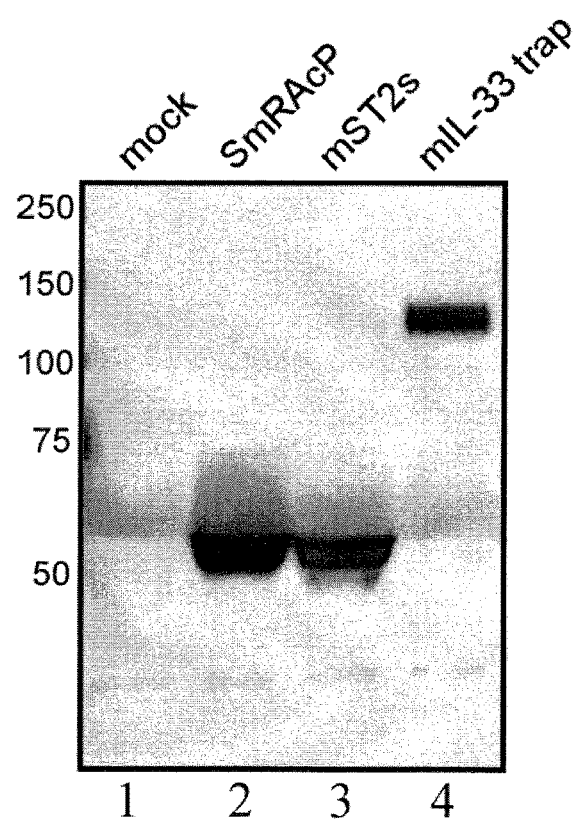

Construction of Expression Vectors pEF-mST2L and pEF-SmIL1RAcP were constructed as follows. Total RNA was isolated from the mouse macrophage cell line Mf4/4 using TRIZOL® reagent (Sigma-Aldrich). First strand cDNA was synthesized by reverse transcription (iScript, BioRad). mST2L was PCR amplified with TAQ DNA polymerase (Table 1: primers 1 and 3) and ligated in pGEM-Teasy, resulting in pGEM-mST2L. The mST2L cDNA was isolated by XbaI digestion from pGEM-mST2L and cloned in the XbaI site of pEF6-myc/HisA (Invitrogen) to obtain the expression vector pEF-mST2L. The coding sequence of soluble mIL1-RAcP was PCR amplified with TAQ DNA polymerase (Table 1: primers 4 and 5). After digestion with EcoRI and XbaI, the PCR fragment was ligated in the EcoRI/XbaI opened pEF6-myc/HisA vector to obtain the expression plasmid pEF-SmIL1RAcP.

pEF-mST2s was constructed as follows: mST2s was PCR amplified from Origene clone MC204735 (Table 1: primers 1 and 2) and ligated in the XbaI site of pEF6-myc/HisA, resulting in pEF-mST2s.

pEF-mIL33traps were constructed as follows: Soluble mouse ST2 without the signal sequence (amino acids 27-337) was PCR amplified from pEF-mST2s (Table 1: primers 6 and 7) and digested with PstI and EcoRV. A linker sequence of repeating Gly-Gly-Ser triplets was PCR amplified from pCLG-Duba (BCCM/LMBP number 6610), which contains 20 Gly-Gly-Ser repeats, with primers 8 and 9 (Table 1) and digested with XbaI and PstI. Both DNA fragments were cloned by a three-way ligation reaction in the XbaI/PmeI-digested pEF-SmIL1RAcP vector. Three constructs with different linker length (20, 12 or 8 Gly-Gly-Ser repeats) were obtained.

All constructs were confirmed to be correct by DNA sequencing analysis.

The expression vector for murine IL1-RAcP (pCR4-Flag-mIL1RAcP) was kindly provided by Dr. Sophie Janssens from our department.

pEF-hST2s was constructed as follows: hST2s was PCR amplified from pEF-BOS-hST2s (Table 1: primers 10 and 11) and ligated in the BamHI/NotI opened pEF6-myc/HisA vector, resulting in pEF-hST2s. DNA sequencing of these constructs revealed a PCR-induced point mutation, leading to the conversion of a methionine to a lysine at position 13 in the signal peptide of hST2s (M13K).

pEF-ShIL1RAcP was constructed as follows: The coding sequence of soluble hIL1-RAcP was PCR amplified with TAQ DNA polymerase (Table 1: primers 12 and 13) from a human spleen cDNA library. After digestion with EcoRI and XbaI, the PCR fragment was ligated in the EcoRI/XbaI opened pEF6-myc/HisA vector to obtain the expression plasmid pEF-ShIL1 RAcP.

pEF-hIL33traps were constructed as follows: Soluble human ST2 without the signal sequence (amino acids 19-328) was PCR amplified from pEF-hST2s (Table 1: primers 14 and 7) and digested with NsiI (partially) and EcoRV. A linker sequence of repeating Gly-Gly-Ser triplets was PCR amplified from pCLG-Duba (BCCM/LMBP number 6610), which contains 20 Gly-Gly-Ser repeats, with primers 8 and 9 (Table 1) and digested with XbaI and PstI. Both DNA fragments were cloned by a three-way ligation reaction in the XbaI/PmeI-digested pEF-ShIL1RAcP vector. Two constructs with different linker length (20 or 8 Gly-Gly-Ser repeats) were obtained. DNA sequencing of the hIL33trap constructs revealed a PCR-induced point mutation, leading to the conversion of a lysine to an arginine at position 41 of the hST2s part of the proteins (K41R).

pEF-BOS-hST2s and pEF-BOS-hST2L constructs were kindly provided by Prof. Luke O'Neill (Trinity College Dublin, Ireland).

changed and the cells were incubated for 72 hours at 37° C. The conditioned medium fractions were analyzed by Western blotting with an anti-His antibody (Roche) for the presence of the secreted recombinant proteins and used for IL-33-blocking experiments.

Purification of Recombinant mST2s and mIL33Trap Proteins

Recombinant mouse ST2s and IL33trap proteins containing a myc/His6 tag at the C terminus were purified by standard chromatographic methods. Briefly, HEK293T cells were transiently transfected with pEF-mST2s or pEF-mIL33trap using the calcium-phosphate method. Sixteen hours after transfection, the medium was changed and the cells were cultured for 48 hours in serum-free DMEM medium. The secreted recombinant proteins in the medium fractions were concentrated by diafiltration and purified by metal affinity chromatography using nickel-Sepharose. After a final gel-filtration over a SUPERDEX® 200 column, the purified proteins were stored in PBS at −80° C. Protein concentrations were determined by Micro BCA protein assay and the purity of the purified proteins were assayed by SDS-PAGE and Western blotting using an anti-His antibody (Roche).

TABLE 1

Sequences of the primers used for the construction of expression vectors.

| primer number | primer name | Sequence (5'-3') | SEQ ID NO: |
|---|---|---|---|
| 1 | fw-Xba-ST2 | AGTTCTAGAATGATTGACAGACAGAGAATGG | 8 |
| 2 | rev-Xba-ST2 | TAATCTAGAAGCAATGTGTGAGGGACACTC | 9 |
| 3 | rev-Xba-ST2L | AATTCTAGAAAAGTGTTTCAGGTCTAAGCATG | 10 |
| 4 | F-solmIL1RAP-Eco | TTCGAATTCATGGGACTTCTGTGGTATTTG | 11 |
| 5 | R-solmIL1RAP-Xba | AGATCTAGACAGAGTCATCGGCTCGGTG | 12 |
| 6 | Fw-Pst-mST2extra | CAGCTGCAGAGTAAATCGTCCTGGGGTCTG | 13 |
| 7 | Rev-ST2-myc-His_Pme-EcoRV | ATCGATATCGTTTAAACTCAATGGTGATGGTG | 14 |
| 8 | F-20xGGS-Xba | AGATCTAGAGGAGGGAGTGGTGGCTCTGG | 15 |
| 9 | R-20xGGS-Pst | CAGCTGCAGGCTCCCACCACTCCCTCCAG | 16 |
| 10 | Fw-BamHI-hST2s | TCCGGATCCATGGGGTTTTGGATCTTAGCAATTC | 17 |
| 11 | R-Not-hST2s (F328) | TAAGCGGCCGCGAGAAACACTCCTTACTTGGATTTTTC | 18 |
| 12 | Fw-EcoRI-hRAcP | TTCGAATTCATGACACTTCTGTGGTGTGTAGTG | 19 |
| 13 | Rev-XbaI-ShRAcP (Q356) | ATTTCTAGACTGACCGCATCTATTACCTTTCTG | 20 |
| 14 | Fw-NsiI-hST2s (K19) | CATATGCATAAGTTTAGTAAACAATCATGGGG | 21 |

Expression of Soluble Receptors and Receptor Fusion Proteins

HEK293T cells were cultured in DMEM supplemented with 10% FCS and Pen/Strep. $2 \times 10^5$ HEK293T cells were seeded in six-well plates and transfected the next day by calcium phosphate precipitation with the desired expression vectors. Four hours after transfection, the medium was In vitro Bioassay HEK293T cells were cultured in DMEM supplemented with 10% FCS and Pen/Strep. $4 \times 10^4$ HEK293T cells were seeded in 24-well plates and transfected the next day by calcium phosphate precipitation with expression vectors for IL-33Ra (pEF-mST2L) and the co-receptor (pCR4-Flag-mIL1RAcP) and an NF-kB-luciferase reporter plasmid, rendering the cells responsive to IL-33. For experiments with human IL-33, HEK293T cells were rendered responsive by transfecting pEF-BOS-hST2L. The co-transfected beta-galactosidase reporter plasmid pAct-bgal served as an internal control to normalize the luciferase readout. Four hours after transfection, the medium was changed and the cells were left overnight. Twenty-four hours after transfection, the cells were stimulated for five hours with a fixed concentration of mouse IL-33 (R&D Systems) or human IL-33 (produced in *Pichia pastoris*) or left untreated. For IL-33-blocking experiments, the IL-33-containing medium was pre-incubated with the indicated purified recombinant proteins or conditioned medium fractions for 30 minutes at room temperature on a rotating wheel prior adding to the cells. Finally, luciferase activity in the cell lysates was measured by chemiluminescence.

Example 1: Construction and Purification of the Mouse IL-33 Trap

Figure 2:
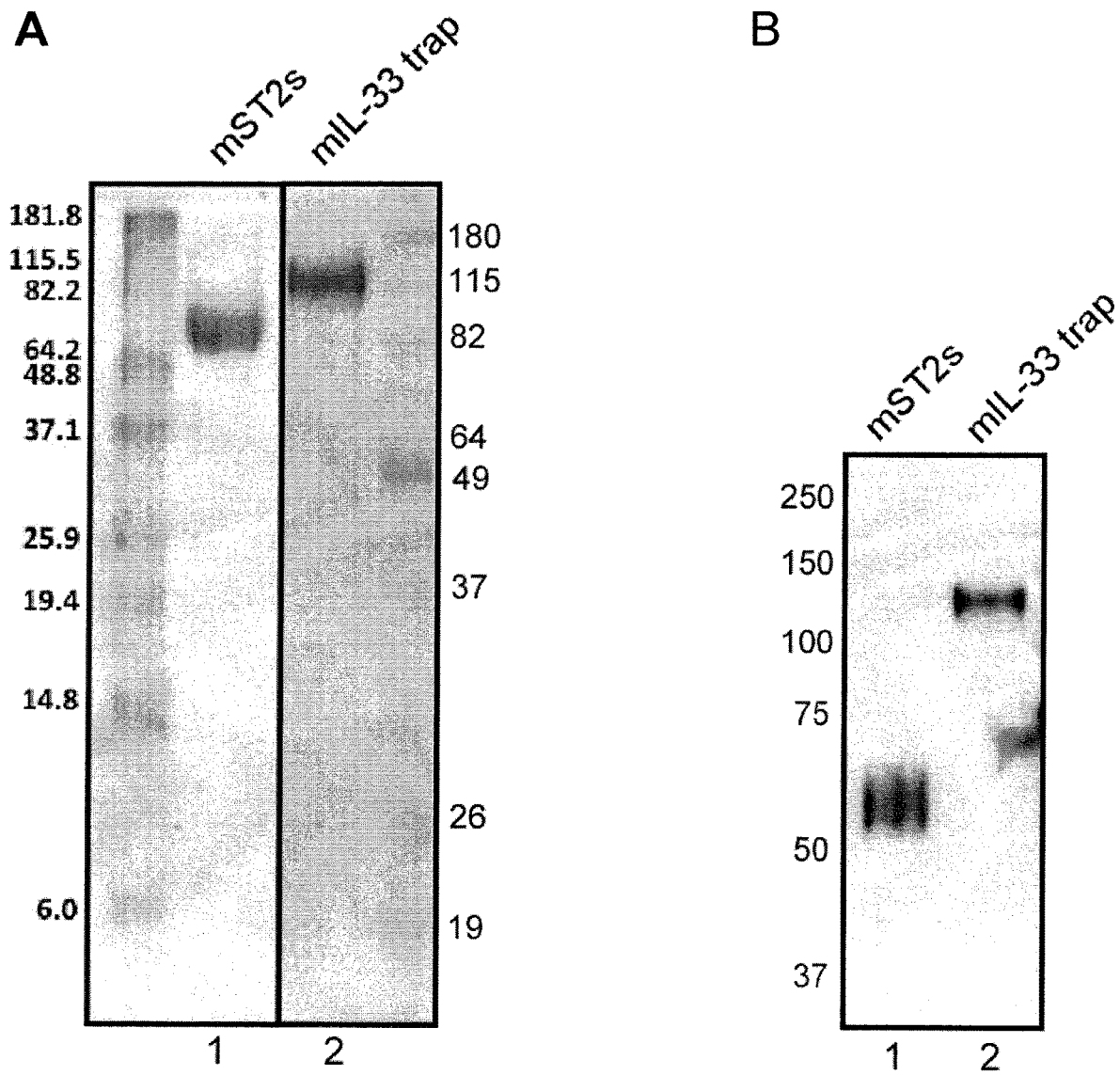
FIG. 2: Purified mST2s and mIL33trap proteins. Panel A, SDS-PAGE analysis and COOMASSIE® blue staining of purified mST2s protein (lane 1) and mIL33trap protein (lane 2). Protein sizes are indicated in kDa at the left and right. Panel B, Western blot analysis of the same purified proteins. One hundred nanograms of each protein (lane 1: mST2s, lane 2: mIL33trap) was separated by SDS-PAGE, blotted on nitro-cellulose membrane and visualized with an anti-His6 antibody. Protein size is indicated in kDa at the left.

The engineered mouse IL-33 trap is encoding a fusion protein consisting of the soluble isoforms (extracellular domains) of the murine IL-1RAcP and ST2 (IL-33Ra) receptor chains, separated by a flexible Gly-Gly-Ser linker (FIG. 1, Panel A). The expressed protein contains the natural signal peptide of the IL-1RAcP, leading to the secretion of the recombinant protein into the medium fraction when expressed in mammalian cells. The C-terminal myc/His6 tag allows easy detection and purification of the protein from conditioned medium of transfected cells (FIG. 1, Panel B).

mST2s and mIL33trap proteins were purified from conditioned medium of transiently transfected HEK293T cells by standard chromatographic methods to a purity of approximately 95%, judged by COOMASSIE® blue staining (FIG. 2, Panel A).

Example 2: mIL33Trap is a Potent Inhibitor of IL-33 In Vitro

The potential of the engineered mIL33trap to block the cytokine activity of IL-33 was evaluated in an in vitro bioassay. mIL33trap proteins were compared to mST2s or the combination of mST2s and SmIL1RAcP in their ability to block IL-33-induced NF-kB luciferase reporter activation in mST2L/mIL-1RAcP-transfected HEK293T cells. Stimulation of the transfected cells with mIL-33 strongly activates NF-kB reporter expression. Pre-incubation of IL-33 with mST2s reduces its ability to activate NF-κB, which is slightly stronger in the presence of the soluble co-receptor SmIL-1RAcP. The soluble co-receptor alone, however, has no effect on the activity of IL-33. In contrast, pre-incubation with mIL33trap proteins blocked IL-33 activity significantly stronger than mST2s or the combination mST2s/SmIL1-RAcP (FIG. 2). Amounts of SmIL1-RAcP, mST2s and mIL33trap were comparable (FIG. 1, Panel B). Amounts of the three different mIL33trap proteins (20×GGS, 12×GGS and 8×GGS with different linker length of 20, 12 or 8 Gly-Gly-Ser repeats, respectively) were comparable.

For purification and further experiments, the fusion protein with the shortest linker (8×GGS) was chosen and designated mIL33trap.

Figure 3:
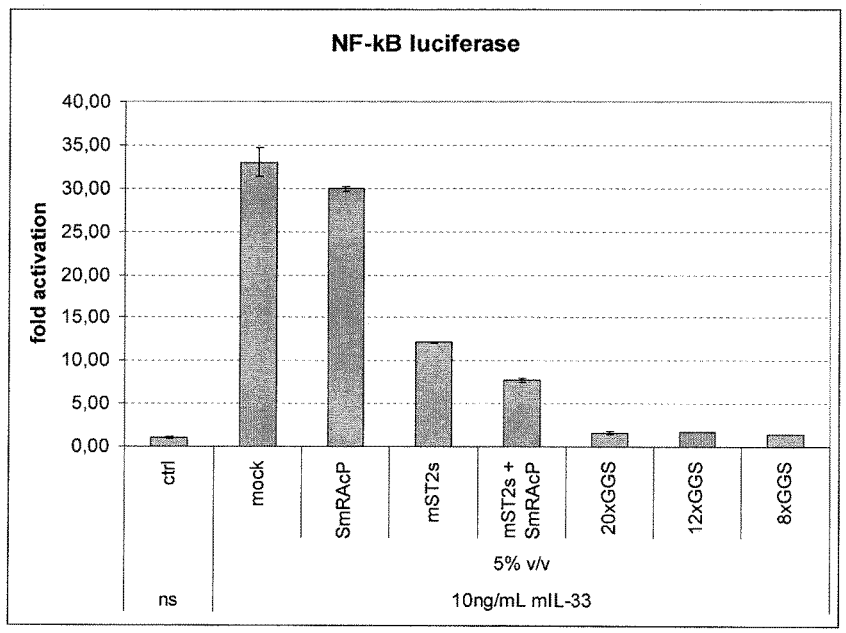
FIG. 3: mIL33trap proteins are highly potent inhibitors of IL-33 activity in vitro. Panel A, Inhibition of IL-33-induced NF-kB activity by IL-33-blocking proteins. mIL-33-containing medium was preincubated with conditioned medium from various protein-producing HEK293T cells (5% v/v) for 30 minutes prior to adding to mST2L/mIL-1RAcP-transfected HEK293T cells. Fold activation of NF-kB activity was calculated relative to transfected, not stimulated (ns) cells. Panel B, Inhibition of IL-33-induced NF-kB activity by purified IL-33-blocking proteins. mST2L/mIL-1RAcP-transfected HEK293T cells were stimulated with 0.5 nM mIL-33 (second dark grey bar) or with 0.5 nM mIL-33, which was preincubated with various concentrations of mST2s (light gray bars) or mIL33trap protein (medium gray bars). Fold activation of NF-kB activity was calculated relative to transfected, not stimulated (ns) cells.
Figure 3:
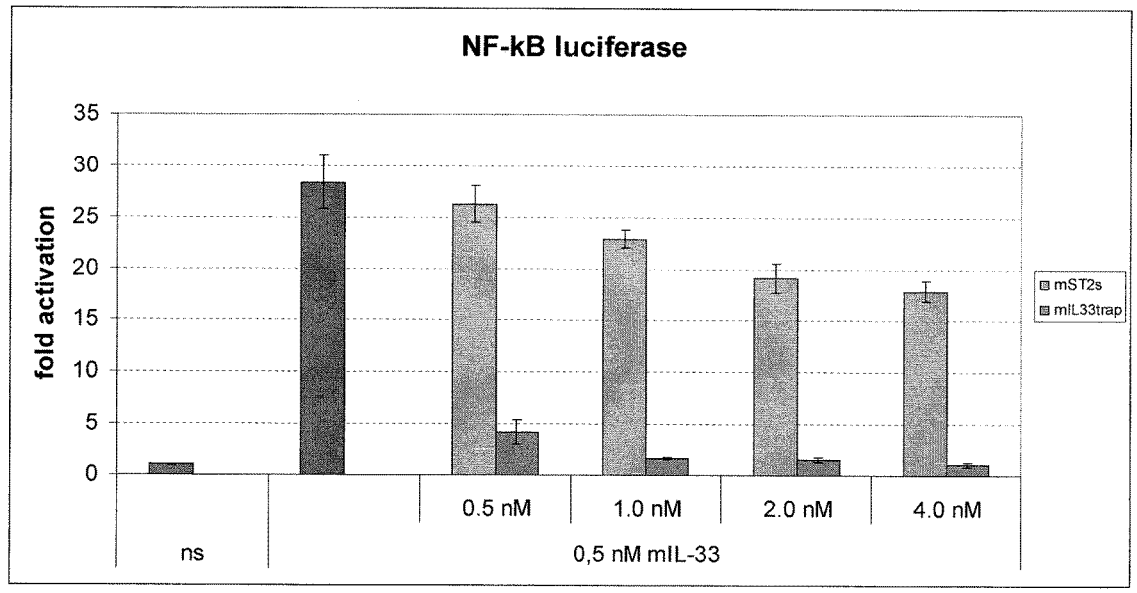

For a more quantitative analysis, the same in vitro bioassay was performed with purified mST2s and IL33trap proteins (FIG. 2) as IL-33 blockers. In this experiment (FIG. 3, Panel B), where IL-33 blocking was performed at low molar ratios, mST2s was a rather weak inhibitor of IL-33 activity. Strikingly, mIL33trap was a high-affinity IL-33 blocker, which almost completely inhibited IL-33-induced NF-kB activation even at equimolar ratio.

Example 3: hIL33Trap is a Potent Inhibitor of IL-33 in Vitro

Figure 4:
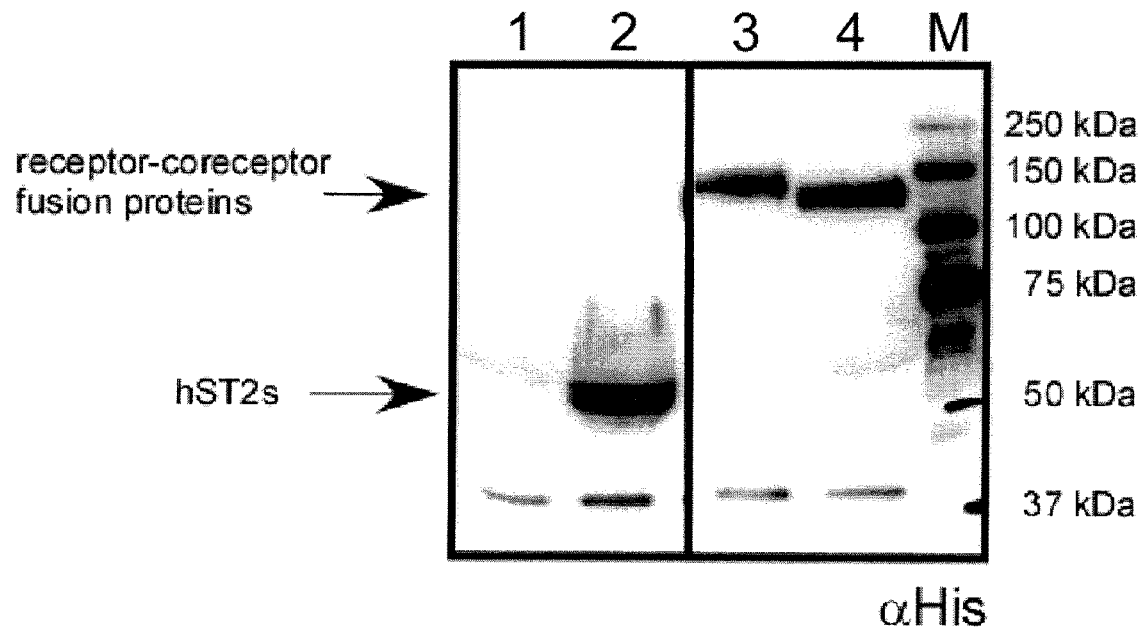
FIG. 4: Potent inhibition of hIL-33 activity by hIL33trap protein in vitro. Panel A, Western blot analysis of secreted proteins. Conditioned medium from HEK293T cells transiently transfected with empty vector (lane 1), pEF-hST2s (lane 2), pEF-hIL33trap (20×GGS) (lane 3) or pEF-hIL33trap (8×GGS) (lane 4) were analyzed by Western blotting with an anti-His6 antibody. Protein size is indicated in kDa at the left. Due to glycosylation of the expressed proteins, the apparent size is bigger than their theoretical weight. Panel B, Inhibition of hIL-33-induced NF-kB activity by hIL-33-blocking proteins. hIL-33-containing medium was preincubated with conditioned medium from various protein-producing HEK293T cells (10% v/v) for 30 minutes prior adding to hST2L-transfected HEK293T cells. Fold activation of NF-kB activity was calculated relative to transfected, not stimulated (ns) cells.
Figure 4:
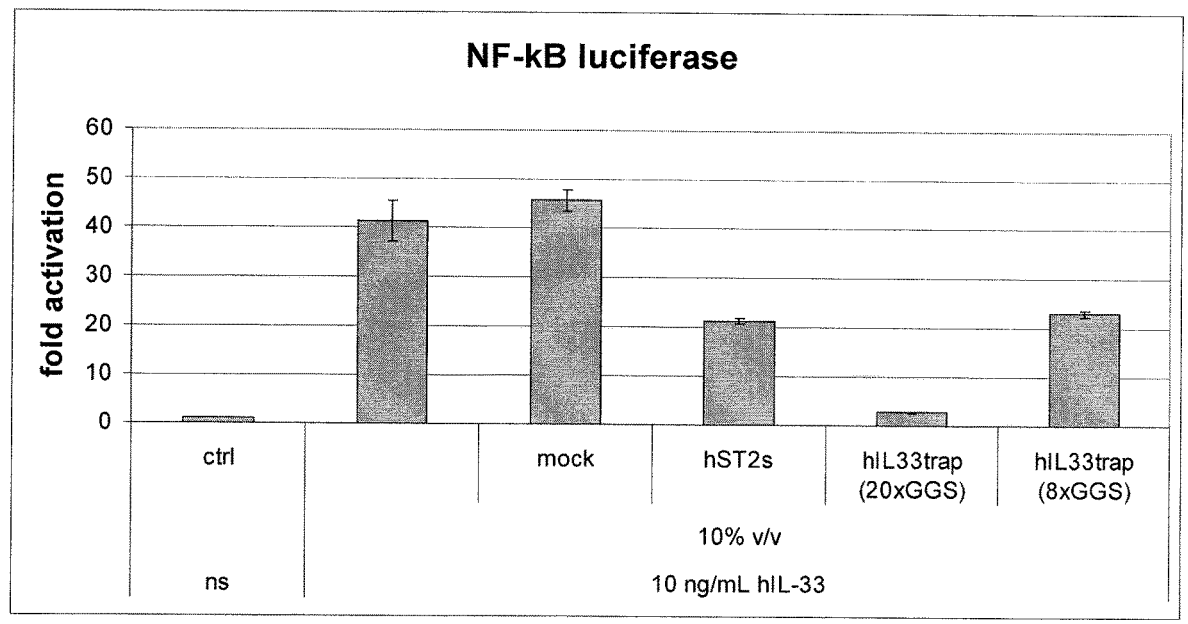

The potential of the engineered hIL33trap to block the cytokine activity of IL-33 was evaluated in an in vitro bioassay. hIL33trap proteins were compared to hST2s in their ability to block IL-33-induced NF-kB luciferase reporter activation in hST2L/hIL-1RAcP-transfected HEK293T cells. Stimulation of the transfected cells with hIL-33 strongly activates NF-kB reporter expression. Pre-incubation of IL-33 with hST2s reduces its ability to activate NF-κB. The soluble co-receptor alone, however, has no effect on the activity of IL-33. Pre-incubation with hIL33trap proteins blocked IL-33 activity significantly stronger than hST2s (FIG. 4, Panel B). In contrast to mIL-33 trap proteins, hIL-33-blocking activity of the hIL33trap proteins is critically dependent on the length of the Gly-Gly-Ser linker: 8×GGS-containing hIL-33 trap is not more active than hST2s, whereas 20×GGS-containing hIL-33trap is much more potent than hST2s. Amounts of hST2s (FIG. 4, Panel A, lane 2) and the two different hIL33trap proteins (20×GGS and 8×GGS with different linker length of 20 or 8 Gly-Gly-Ser repeats, respectively) were comparable (FIG. 4, Panel A, lanes 3 and 4).

Example 4: mIL33Trap is a Potent Inhibitor of Allergic Asthma

To address the in vivo effect of mIL33trap in allergic asthma (an IL-33-mediated disease), a mouse model was used in which all features of asthma are induced by the allergen house dust mite (HDM). Mice were sensitized intratracheally on day 0 with 1 µg HDM extracts. To ensure the proper blockade of IL-33 locally in the lungs, some mice were administered intratracheally, either with 40 µg of soluble mST2s or with 40 µg of mIL33trap (8×GSS linker). On days 7 to 11, mice were re-exposed intranasally to HDM to induce asthma features. On day 14, the bronchoalveolar lavage (BAL) fluids were collected and analyzed for the presence of inflammatory cells (neutrophils, lymphocytes and eosinophils). Mice that were sensitized and challenged with HDM showed a strong recruitment of eosinophils and lymphocytes in the BAL fluids, indicative of allergic asthma development. Mice that were also administered with soluble mST2s showed a 45% reduction in the number of eosinophils and a 24% reduction in the number of lymphocytes, compared to untreated mice. However, mIL33trap administration induced a 55% reduction in the number of eosinophils and a 46% reduction in the number of lymphocytes, compared to untreated mice.

In conclusion, both soluble mST2s and mIL33trap had the potential to reduce features of allergic asthma but mIL-33trap is significantly more potent than mST2s (most pronounced for the inhibitory effect on lymphocyte recruitment to the airways of asthmatic mice).

REFERENCES

Chackerian, A. A., E. R. Oldham, E. E. Murphy, J. Schmitz, S. Pflanz, and R. A. Kastelein (2007). IL-1 receptor accessory protein and ST2 comprise the IL-33 receptor complex. *J. Immunol.* 179, 2551-2555.

Haraldsen, G., J. Balogh, J. Pollheimer, J. Sponheim, and A. M. Kuchler (2009). Interleukin-33—cytokine of dual function or novel alarmin? *Trends Immunol.* 30, 227-233.

Lamkanfi, M. and V. M. Dixit (2009). IL-33 raises alarm. *Immunity* 31, 5-7.

Miller, A. M. (2011). Role of IL-33 in inflammation and disease. *J. Inflammation* 8, 22-33.

The invention claimed is:

1. A monomeric fusion protein comprising a soluble IL-33 receptor and a soluble IL-1RAcP, wherein the fusion protein comprises an amino acid sequence selected from the group consisting of SEQ ID NO:6 and SEQ ID NO:7.

2. A pharmaceutical composition, comprising: the monomeric fusion protein of claim 1, and a suitable excipient.

3. A monomeric fusion protein comprising a soluble IL-33 receptor and a soluble IL-1RAcP, wherein the fusion protein comprises the amino acid sequence of SEQ ID NO:6.

4. A pharmaceutical composition, comprising: the monomeric fusion protein of claim 3, and a suitable excipient.

* * * * *